(12) United States Patent
Armstrong et al.

(10) Patent No.: US 6,417,247 B1
(45) Date of Patent: *Jul. 9, 2002

(54) POLYMER/CERAMIC COMPOSITES

(76) Inventors: Beth L. Armstrong, 6817 W. Wernett Rd., Pasco, WA (US) 99301; Allison A. Campbell, 1515 W. 16th, Kennewick, WA (US) 99337; Anna Gutowska, 450 Mateo Ct.; Lin Song, 464 Mainmast Ct., both of Richland, WA (US) 99352

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/079,884

(22) Filed: May 15, 1998

Related U.S. Application Data (60) Provisional application No. 60/062,108, filed on Oct. 14, 1997.

(51) Int. Cl.[7] ............................. A61F 2/02; A61K 47/36; A61K 47/34
(52) U.S. Cl. ................. 523/115; 424/423; 424/426; 523/113; 523/114; 523/218; 524/55; 524/555; 524/556; 524/916; 524/27; 536/20; 536/114
(58) Field of Search .......................... 524/55, 555, 556, 524/916; 523/113, 114, 115, 218; 424/423, 426; 536/114, 20

(56) References Cited

U.S. PATENT DOCUMENTS

| | | | | |
|---|---|---|---|---|
| 4,382,792 A | * | 5/1983 | Smith et al. ................ | 523/118 |
| 4,478,882 A | | 10/1984 | Haslam et al. ................ | 424/78 |
| 4,631,188 A | * | 12/1986 | Stoy et al. ..................... | 424/81 |
| 4,722,948 A | * | 2/1988 | Sanderson ................... | 523/115 |
| 4,938,763 A | * | 7/1990 | Dunn et al. .................. | 424/426 |
| 5,089,606 A | * | 2/1992 | Cole et al. .................... | 536/54 |
| 5,204,382 A | * | 4/1993 | Wallace et al. .............. | 523/115 |
| 5,252,318 A | * | 10/1993 | Joshi et al. .................. | 424/422 |
| 5,278,201 A | * | 1/1994 | Dunn et al. | |
| 5,352,715 A | * | 10/1994 | Wallace et al. .............. | 523/115 |
| 5,405,390 A | * | 4/1995 | O'Leary et al. .............. | 623/16 |
| 5,603,955 A | * | 2/1997 | Gehrke et al. ............... | 424/484 |
| 5,639,796 A | * | 6/1997 | Lee ............................. | 523/113 |
| 5,658,593 A | * | 8/1997 | Orly et al. ................... | 424/426 |
| 5,702,716 A | * | 12/1997 | Dunn et al. .................. | 523/113 |
| 5,922,025 A | * | 7/1999 | Hubbard ...................... | 523/115 |
| 5,945,115 A | * | 8/1999 | Dunn et al. .................. | 523/113 |
| 6,001,394 A | * | 12/1999 | Daculsi et al. ............... | 424/426 |

FOREIGN PATENT DOCUMENTS

| | | | | |
|---|---|---|---|---|
| DE | 3531144 | * | 3/1986 | .................. 523/115 |
| EP | 0 298 501 A2 | | 7/1988 | ............. A61K/6/06 |
| WO | 05911 | * | 2/1997 | |

* cited by examiner

Primary Examiner—Peter Szekely
(74) Attorney, Agent, or Firm—Paul W. Zimmerman; Stephen R. May (57) ABSTRACT

The present invention provides a composition which comprises a polymer or polymer solution that forms a gel under controlled parameters and a ceramic matrix, the composition being fluid under non-physiological conditions and non fluid under physiological conditions. Polymers may be resorbable or non-resorbable, natural or synthetic and the solution aqueous or non-aqueous. Preferred polymers are poly saccharides, polyamides or polyamino acids, however any polymer or polymer solution that is biologically compatible and that is fluid under nonphysiological conditions and increases in viscosity under physiological conditions is suitable.

15 Claims, 12 Drawing Sheets

POLYMER/CERAMIC COMPOSITES

RELATED APPLICATION

This application claims priority to provisional patent application Ser. No. 60/062,108 filed Oct. 14, 1997.

TECHNICAL FIELD

The present invention relates to a method for constructing an implant by placement of a paste comprising a stimuli sensitive polymer solution carrying a biocompatible ceramic component which hardens under physiological conditions to form a solid implant. The implant may also include a therapeutic agent or a radioisotope.

BACKGROUND OF THE INVENTION

Many researchers have experimented with drug delivery vehicles based on the use of controlled release implant materials. Others have sought to provide improved implants for filling in tissue losses from age or trauma, to hard or soft tissues. Calcium phosphate pastes have been suggested as bone and dental fillers. Gels have been used as control release devices and as fillers. Representative studies are discussed below.

In U.S. Pat. No. 4,188,373, certain polyols are used in aqueous compositions to provide thermally gelling aqueous systems. In these systems, the sol-gel transition temperature can be changed by manipulating the concentration of polymer. In U.S. Pat. Nos. 4,474,751; '752; '753; and 4,478,822 drug delivery systems are described which utilize thermosetting gels. In these systems, both the gel transition temperature and/or the rigidity of the gel can be modified by adjustment of the pH and/or the ionic strength, as well as by the concentration of the polymer. U.S. Pat. Nos. 4,883,660; 4,767,619; 4,511,563; 4,861,760, and 4,911,926 also disclose gels that deliver pharmaceutical compositions.

In U.S. Pat. No. 4,895,724, compositions are disclosed for the controlled release of pharmacological macromolecular compounds contained in a matrix of chitosan. Chitosan can be cross-linked utilizing aldehydes, epichlorohydrin, benzoquinone, etc. In U.S. Pat. No. 4,795,642, discloses gelatin-encapsulated, controlled-release pharmaceutical compositions, wherein the gelatin encloses a solid matrix formed by the cation-assisted gelation of a liquid filling composition incorporating a vegetable gum together with a pharmaceutically-active compound. The vegetable gums are disclosed as polysaccharide gums such as alginates which can be gelled utilizing a cationic gelling agent such as an alkaline earth metal cation.

Osmotic drug delivery systems are disclosed in U.S. Pat. No. 4,439,196 which utilize a multi-chamber compartment for holding osmotic agents, adjuvants, enzymes, drugs, pro-drugs, pesticides, and the like. These materials are enclosed by semipermeable membranes so as to allow the fluids within the chambers to diffuse into the environment into which the osmotic drug delivery system is in contact. U.S. Pat. No. 5,587,175 teaches a process for forming a protective corneal shield or an ablatable corneal shield or mask in situ comprising administering to the eye of a mammal an aqueous composition capable of being gelled in situ to produce an hyper osmotic, hypo osmotic, or iso osmotic aqueous gel having a controlled pH, said aqueous composition, including at least one film forming polymer; and gelling said film forming polymer in situ to form said protective corneal shield or ablatable corneal shield or mask.

U.S. Pat. No. 3,949,073 discloses injectable atelocollagen solutions which precipitate at body temperature, thus leading to the formation of fibers which remain at the injection site whereas the excipient is progressively resorbed. U.S. Pat. No. 5,658,593 in one embodiment provides micro capsules based on atelocollagen optionally mixed with a glycosaminoglycan such as chondroitin-4-sulfate, the micro capsules containing granules of hydroxyapatite in suspension in a viscous bio compatible carrier solution of a gel of atelocollagen optionally mixed with a glycosaminoglycan, in particular chondroitin-4-sulfate, for use as a filler material in forming injectable implants.

U.S. Pat. No. 5,626,861 teaches a method for the fabrication of three-dimensional macro porous polymer matrices for use as bone graft or implant material was developed. The composites are formed from a mixture of biodegradable, bio compatible polymer and hydroxyapatite (HA), a particulate calcium phosphate ceramic. The method leaves irregular pores in the composite between 100 and 250 microns in size by formation of a solid gel comprising a soluble material and dissolving the material to form voids in the gel. In a preferred embodiment, implants are composed of a 50:50 poly(lactide-co-glycolide) (PLGA) polymer and reinforced by hydroxyapatite. Mechanical and histological analysis showed the matrix fabricated by this method to be structurally and mechanically similar to cancellous bone. Prior to degradation, pure polymer specimens exhibited an elastic modulus of 293 MPa and specimens which were 50% HA by weight exhibited a modulus of 1459 MPa. After six weeks of degradation under physiological conditions, the reinforcing effect of ceramic loading had diminished. Modulus of polymer matrices at all HA load levels had decreased sharply to approximately 10 MPa. Mean macro- and micro pore diameters of the polymer specimens were 100 mu m and 20 mu m respectively and remained constant throughout degradation. The implants are hardened, leached and then implanted into the subject where they are slowly degraded by natural bodily action over a period of time. The implant size and shape must be predetermined and thus may not perfectly fit the site to be repaired.

B. R. Constantz, et als, 1995, Skeletal Repair by in Situ Formation of the Mineral Phase of Bone, *Science,* 267:1796–1799. Discloses a process for the surgical implantation of a paste that hardens in minutes under physiological conditions. The mixture comprises a mixture of calcium phosphates and sodium phosphate, and hardens due to the crystallization of dahlite, not mediated by a stimulus setting gel. The mixture hardens regardless of whether it is placed in the body. The paste is a hydroxyapatite precursor and does not include gel components.

B. Flautre, et als, 1996, Evaluation of Hydroxyapatite Powder Coated with Collagen as an Injectable Bone Substitute: Microscopic Study in Rabbit, *J. Materials Science-:Materials in Medicine,* 7:63–67, discloses an injectable mix of hydroxyapatite and collagen but there is no disclosure of providing a stimulus response setting material. The group uses HA and atecollegen and chondrotin-4-sulfate formulated as micro spheres, similar to the patents discussed above. There is no provision for a gel which forms in response to a stimulus provided by exposure to the environment of the body, and there is no provision for differential loss of materials to provide a porous matrix. A further study by the same group, G. Pasquier, et als, 1996, Injectable Percutaneous Bone Biomaterials: an Experimental Study in a Rabbit Model, *J. Materials Science:Materials in Medicine,* 7:683–690, discloses mixtures comprising an orthopaedic acrylic cement (polymethylmethacrylate ("PMMA")) and HA as well as HA and collagen. The PMMA was used as a reference bio-inert material. There is no disclosure of a stimulus setting gel for producing a composite which only hardens in response to a stimulus supplied by the body.

M. Ito, et als, 1994, Experimental Development of a Chitosan-bonded β-Tricalcium Phosphate Bone Filling Paste, *Bio-Medical Materials and Eng.*, 4:439–499, discloses a composite of chitosan and tricalcium phosphate containing alkaline oxides of calcium, magnesium or zinc, which provided the conditions to produce setting. Again the material hardens without regard to stimulus supplied from the body. A similar study is reported by M. Takechi, et als, 1996, Non-decay Type Fast-setting Calcium Phosphate Cement Using Chitosan, *J. Materials Science:Materials in Medicine*, 7:317–322. Takechi uses sodium alginate or chitosan as a water insoluble gel to protect calcium phosphate cements from decay during setting under physiological conditions. In these materials the cements set as they normally do and the gel forms in response to the calcium provided by the cement. Again there is no gel formation in response to a physiological stimulus for the composite material.

There is a continuing and long felt need for alternative implant materials for the treatment of damage to bony tissues by injury or disease. The art has not heretofore provided a fluid or shapeable implant material which comprises both a bone growth supporting matrix such as a ceramic matrix, and a stimulus sensitive gel which can be shaped to fill an injury site and then hardens to support the injured tissue during healing. The art has not heretofore provided a polymer/ceramic composite suitable for use in bone repair wherein a stimuli sensitive gel is used as a fluid carrier to place a ceramic matrix into a damaged bony tissue wherein the gel hardens in response to a physiological condition such as temperature, pH, ionic strength and the like in the presence of the ceramic.

SUMMARY OF THE INVENTION

The present invention provides a composition which comprises a polymer or polymer solution that forms a gel under controlled parameters and a ceramic matrix, the composition being fluid under non-physiological conditions and non fluid under physiological conditions. Polymers may be resorbable or nonresorbable, natural or synthetic and the solution aqueous or non aqueous. Preferred polymers are poly-saccharides, random copolymers of (meth)acrylamide derivatives with hydrophillic comonomers, or polyamino acids, however any polymer or polymer solution that is biologically compatible and that is fluid under nonphysiological conditions and increases in viscosity under physiological conditions is suitable. As used in this application, physiological conditions means conditions normally found in a mammalian body such as pH in the range of 4 to 9, ionic strength of around 0.15 or temperature in the range of 35–40° C. Stimuli sensitive gel means a natural or synthetic polymer that increases in viscosity, gels or crosslinks in response to a stimulus such as a change in temperature, pH, ionic strength, light or the like. In contrast to the rigid composites synthetic grafts of the prior art, the compositions of the present invention may be injected at a trauma site, such as a fracture and shaped to fill any voids present, forming and in situ splint and scaffold for the growth of new bone. The composite may also serve as a controlled release device for a therapeutic agent such as a bone growth factor, an antibiotic, a chemotherapy drug, or a cytokine. The composites may include bone morphogenic proteins or other osteoconductive agents. Preferably the composites are formed in such a manner that the final solid implant is porous with macroscopic pores, preferably on the order of 100 to 200 microns in cross section. In an alternative embodiment a near net shape forming composition is employed wherein the polymer is a bio compatible, shear thinning polymer that forms a gel under ambient pressure and a ceramic component carried therein. The shear thinning polymer is one in which the polymer viscosity decreases in response to a stimulus such as ultrasonic vibration or injection.

Alternatively the invention may be viewed as a method of forming a solid implant in a mammalian body which comprises mixing a gel forming component with a ceramic forming component to provide a fluid mixture, placing the fluid mixture into a mammalian body wherein the fluid mixture gels after placement in the mammalian body in response to a stimulus provided by conditions present or induced in the mammalian body. Conditions present in the mammalian body includes normal body temperature, ionic strength, pH and the like. Conditions that can be induced in the body include ultrasonic vibration, externally applied magnetic fields, irradiation from a radiation source or light or other electromagnetic radiation. Preferably the fluid mixture comprises a gel forming polymer, a calcium phosphate ceramic, and a soluble material which will produce voids in the final implant, the voids having an average cross section in the range of 100 to 200 microns. The soluble material is preferably a second polymer which degrades or dissolves relatively rapidly under physiological conditions. Especially preferred polymers dissolve by enzymatic action leaving non toxic, non irritating residues.

DETAILED DESCRIPTION OF THE INVENTION

Mechanisms by which bone may fail include brittle fracture from impact loading and fatigue from constant or cyclic stress. Stresses may act in tension, compression, or shear along one or more of the axes of the bone. A synthetic bone substitute must resist failure by any of these stresses at their physiological levels. A factor of safety on the strength of the implant may ensure that the implant will be structurally sound when subject to hyper physiological stresses. The solid implants of the prior art all require the injured bone to conform to the shape of the implant, requiring invasive surgery, long recovery times, fixation devices inserted into the bone, rigid external or internal splints and ingrowth of bone into the implant ("knitting"). Especially in the elderly, implants may fail due to failure of the bone regrowth and therefore failure of the implant to become joined to the bone. The rigid implant of U.S. Pat. No. 5,626,861 exemplifies the traditional approach of forming the implant ex vivo followed by surgical insertion into the injured bone.

In contrast to the prior art approach, it has now been found that stimuli sensitive gels can be combined with bone precursors such as hydroxyapatite ceramic particles to permit placement of fluid materials into damaged bone. The fluid mixtures form rigid structures on exposure to physiological conditions forming the implant as an integral part of the bony structure. The hardening of the implant may be triggered by any stimuli that can be provided directly or indirectly under physiological conditions. Examples of direct stimuli include temperature, pH, ionic strength, and the like, as they occur in a mammalian body. Examples of indirect stimuli that may be applied under physiological conditions include external heating or cooling, light and other electromagnetic radiation across the broad range of the spectrum, magnetic fields, induced or applied electrical charge or current, and the like.

A variety of bio compatible polymers can be used. The stimulus sensitive polymer may be any bio compatible polymer or copolymer which forms a gel or crosslinked structure in response to a stimulus which may include temperature, pH, ionic strength, solvent composition, sheer stress, light, and the like or a combination of these factors. Preferred polymers are described in co-pending application Ser. No. 08/870,368; Filed Jun. 6, 1997 incorporated herein by reference. Preferred stimulus sensitive polymers are random copolymers of a [meth-]acrylamide derivative and a hydrophilic comonomer, wherein the random copolymer is in the form of a plurality of linear chains having a plurality of molecular weights greater than or equal to a minimum gelling molecular weight cutoff.

The [meth-]acrylamide derivative is an N, N'-alkyl or pyrrolidone substituted [meth-]acrylamide including but not limited to N-isopropyl[meth-]acrylamide, N,N'-diethyl [meth-]acrylamide, N-[meth-]acryloylpyrrolidine, N-ethyl [meth-]acrylamide, and combinations thereof.

The hydrophilic co monomer is any hydrophilic co monomer that polymerizes with the [meth]acrylamide derivative to produce a bio compatible polymer. Preferred hydrophilic co monomers are hydrophilic [meth-]acryl- compounds such as carboxylic acids, [meth-]acrylamide derivatives, and the [meth-]acrylamide esters. The preferred aqueous solvent is deionized water, the solvent may also contain salts. Any biologically acceptable nonaqueous solvent that dissolves the polymer may also be used. In addition to the non-resorbable gelling copolymer of N-isopropyl(meth-) acrylamide and (meth)acrylic acid a biodegradable (resorbable) copolymer exhibiting similar gelation properties may also be used in polymer/ceramic composites that gel in response to physiological conditions. The biodegradable (resorbable) thermally gelling copolymer is obtained by grafting of the oligo(meth-)acrylamide derivative side chains on a biodegradable polymer backbone. Examples of the suitable biodegradable polymers include, polysaccharides and poly(aminoacids). The preferred biodegradable polymers are degraded by enzymatic hydrolysis to non toxic, non irritating residues.

Other polymers include the polysaccharides such as chitosan. Chitosans provide an additional new biodegradable component of polymer-ceramic composites suitable for injectable, resorbable templates for bone tissue regeneration. The rationale of using chitosans for this purpose is based on the fact that chitosan solutions gel in response to pH change from slightly acidic to physiological.

The unique aspect of this novel system is that at pH lower than 6.5 the chitosan-ceramic suspension is a paste-like flowable system and at physiological pH the polymer undergoes a phase transition resulting in entrapment of ceramic component within the reversible gel matrix. Thus, application of pH-reversible gels enables the creation of an implant which may be tailored to any shape of a bone defect needed to be filled. In contrast to the rapid setting gel/cement compositions which harden without regard to whether they are placed into the physiological environment, the present invention hardens on exposure to the physiological conditions that occur only after they are placed into the body. As a consequence, the stimulus response compositions of the invention and practice of the method of the present invention provides a bone filling biomaterial which can be pre-mixed and placed in stages following a sterilization or other treatment without premature setting.

Other polysaccharides such as xanthan gum, (available from Kelco), locust bean gum (available from Aldrich), and carrageenan (available from Aldrich, mainly K-carrageenan) are also useful in the invention. Carrageenan is less preferred because ot was found to cause irritation in an animal model.

Calcium phosphate ceramics are preferred for use as the ceramic component of implants in the repair of bone defects because these materials are non-toxic, non-immunogenic, and are composed of calcium and phosphate ions, the main constituents of bone. Both tricalcium phosphate (TCP) [$Ca_3(PO_4)_2$] and hydroxyapatite (HA) [$Ca_{10}(PO_4)_6(OH)_2$] have been widely studied for this reason. Calcium phosphate implants may be osteoconductive, and have the apparent ability to become directly bonded to bone. As a result, a strong bone-implant interface can be created. However, the mechanical properties of calcium phosphate ceramics make them ill-suited to serve as a structural element. Ceramics are brittle and have low resistance to tensile loading. For this reason the ceramic component is combined with a polymeric component which adds elastic strength to the composition overcoming the shortcomings of the ceramic alone while retaining its positive features.

Other useful ceramics include other calcium or magnesium phosphates, aluminas, and the like. Any nontoxic, non immunogenic ceramic may be substituted for calcium phosphate in special circumstances such as an application wherein resporbtion of the ceramic component is not desired. Calcium phosphate ceramics have a degree of bioresorbability which is governed by their chemistry and material structure. High density HA and TCP implants exhibit little resorption, while porous ones are more easily broken down by dissolution in body fluids and resorbed by phagocytosis. However, TCP degrades more quickly than HA structures of the same porosity in vitro. In fact, HA is relatively insoluble in aqueous environments.

These solubility differences permit the use of mixed calcium phosphate ceramics to control the final structure of the implant by using for example TCP particles sized to be selectively dissolved by bodily fluids and provide voids in the final structure and HA particles sized to crystallize under physiological conditions to provide a mineral matrix to foster bone ingrowth into the implant. Preferably the voids will be in the range of 100 to 200 microns, the preferred size for supporting cell growth. Other non-toxic salts can be substituted for TCP for special purposes in forming voids in the implants. Implants having a macro porous structure which pores on the order of 100 to 200 microns are strongly preferred, although pores may be smaller as in 50 to 150 microns, larger as in 100 to 300 microns, or cover a broader range as in 50 to 500 microns and still provide useful implants.

Bone repaired with the use of a conventional polymeric implant such as those described in U.S. Pat. No. 5,626,861 will be required to be immobilized for between six and eight weeks, the standard procedure for conventional fractures. Where the implants of the present invention permit less invasive surgery and in situ fixation, the healing time may be reduced.

All fractures are subject to static loading even while immobilized in a cast, i.e., there is a load resulting from the weight of the bone itself. In order for the implant to unite bone segments in a fracture, it must have initial strength sufficient to provide the stability necessary for healing to begin. Further, the implant must retain a degree of strength throughout the bone remodeling cycle. Strength retention in the implant is governed by the degradation rate of the polymer in the polymer-ceramic composite. Both high strength retention over time and rapid weakening of the scaffold may be detrimental to the bone repair process. Slow implant resorption can shield immature skeletal tissue from the functional stresses necessary for complete remodeling. Conversely, rapid degradation may prematurely shift load beating to the new bone and cause its collapse. Preparation of example implants is described below to illustrate the invention and not by way of limitation. The examples are not intended to limit the invention which is defined by the claims set out below.

Procedures and Sample Preparation

Xanthan gum solution was prepared by addition of the powder at room temperature with stirring into deionized water or sodium chloride solution with desired ionic strength. The resulting smooth solution was then allowed to stand overnight to release all air bubbles. Solutions of locust beam gum and carrageenan gum were prepared at 70–75° C. and stirred until all powder is dissolved.

Hydroxyapatite(HAP)-xanthan gum and HAP-locust bean gum pastes were prepared by mixing the desired amount of HAP powder (Aldrich) into the polysaccharide solution using either a magnetic stir plate (<30 wt % HAP) or a mechanical stirrer at higher solids loading (>30wt % HAP). To prepare the HAP-carrageenan paste, the carrageenan solution was maintained at 70–75° C. in a water bath during mixing. Rheological measurements such as viscometry, strain sweep and oscillation were conducted using a Bohlin Rheometer.

HAP-polysaccharide paste samples prepared for mechanical testing and dissolution experiments were crosslinked in simulated blood plasma electrolyte solution overnight at room temperature. The simulated blood plasma electrolyte solution contains 3 mM KCl, 1.5 mM MgCl2, 4.2 mM NaHCO3, 1.0 mM KH2PO4, 138 mM NaCl and 2.5 mMCaCl2. It was adjusted to pH 7.4 by the addition of NaOH solution before use.

HAP-polysaccharide paste samples for microstructure and porosity studies were prepared and crosslinked in simulated blood plasma electrolyte solution as described above. They were then cut into small rectangles and quickly frozen in liquid nitrogen, then dried in vacuum at −12° C. for at least 24 hours.

HAP dissolution kinetics was measured using the constant composition method at 25° C. The in-vitro carrageenan leaching experiments were conducted in simulated blood plasma electrolyte solutions and concentration of leached carrageenan was determined by a colormetric method using methylene blue.

EXAMPLE 1

Rheological Studies of Calcium Phosphate-Binder Suspensions

The viscosity of HAP suspensions containing one of the three binders selected was measured as a function of binder properties, binder concentration, HAP solids loading and temperature.

Figure 1:
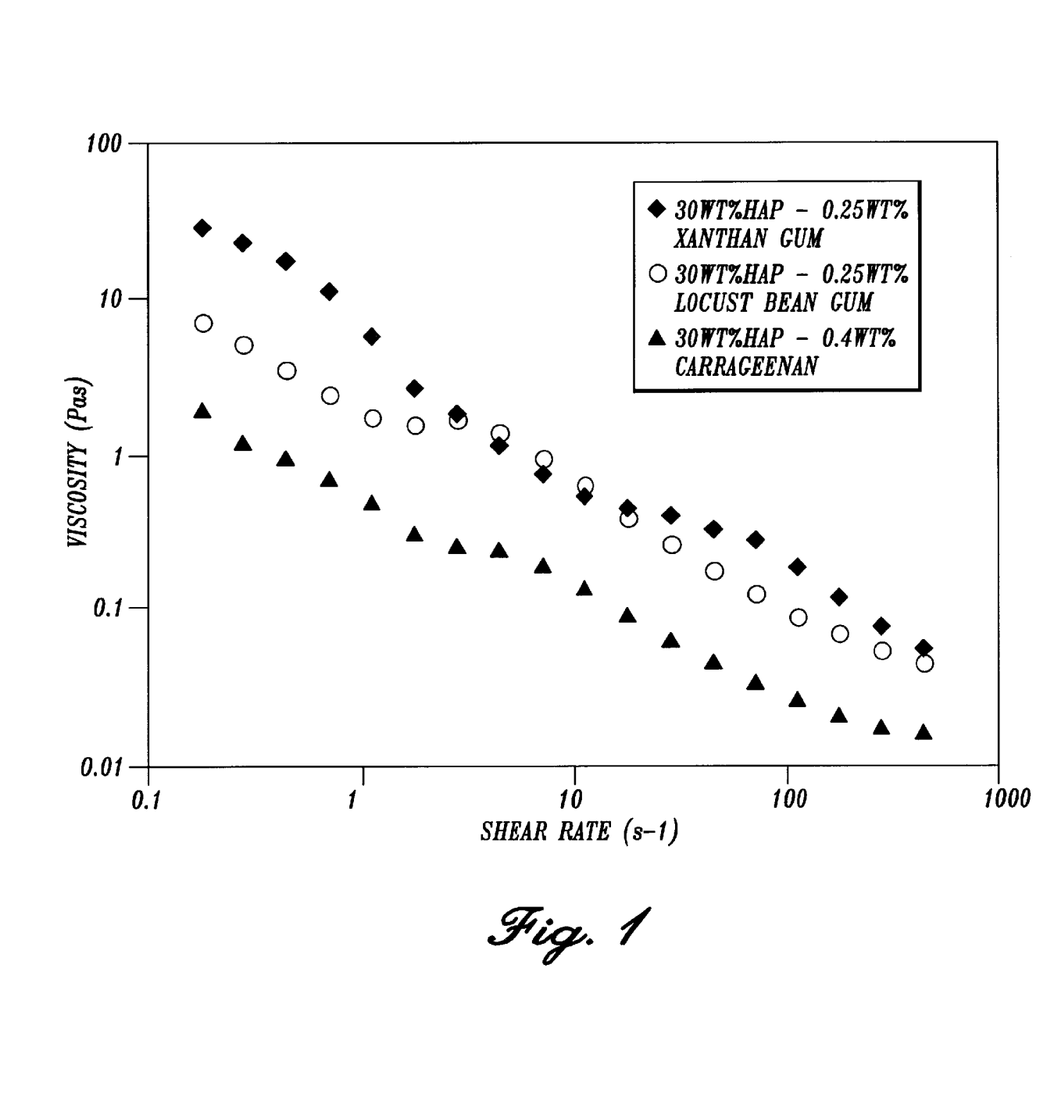
FIG. 1 is a plot of the viscosity of 30 wt % hydroxyapatite (HAP) slurries with different polymers.

Viscosity is a transport property. It must be sufficiently low to facilitate injectability. A shear thinning behavior is desired. This means that at very low shear rates suspended HAP particles remain stationary because the high viscosity of the binder solution was below the yield point. Higher shear rates that are encountered during pouring or during vibration can effectively reduce the viscosity. As shown in FIG. 1, all three slurries containing 30 wt % HAP showed shear thinning behavior. Among them, HAP suspension containing carrageenan had the lowest viscosity even though the carrageenan concentration was higher (0.4 wt %) than the other two binders (0.25 wt %).

Figure 2:
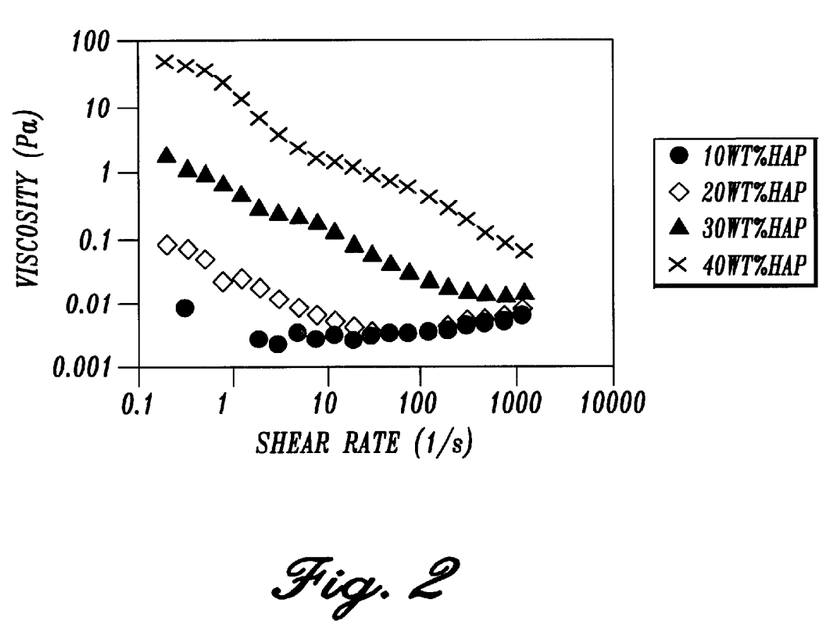
FIG. 2 is a plot of solids loading effect on the viscosity of HAP in 0.4 wt % carrageenan.
Figure 3:
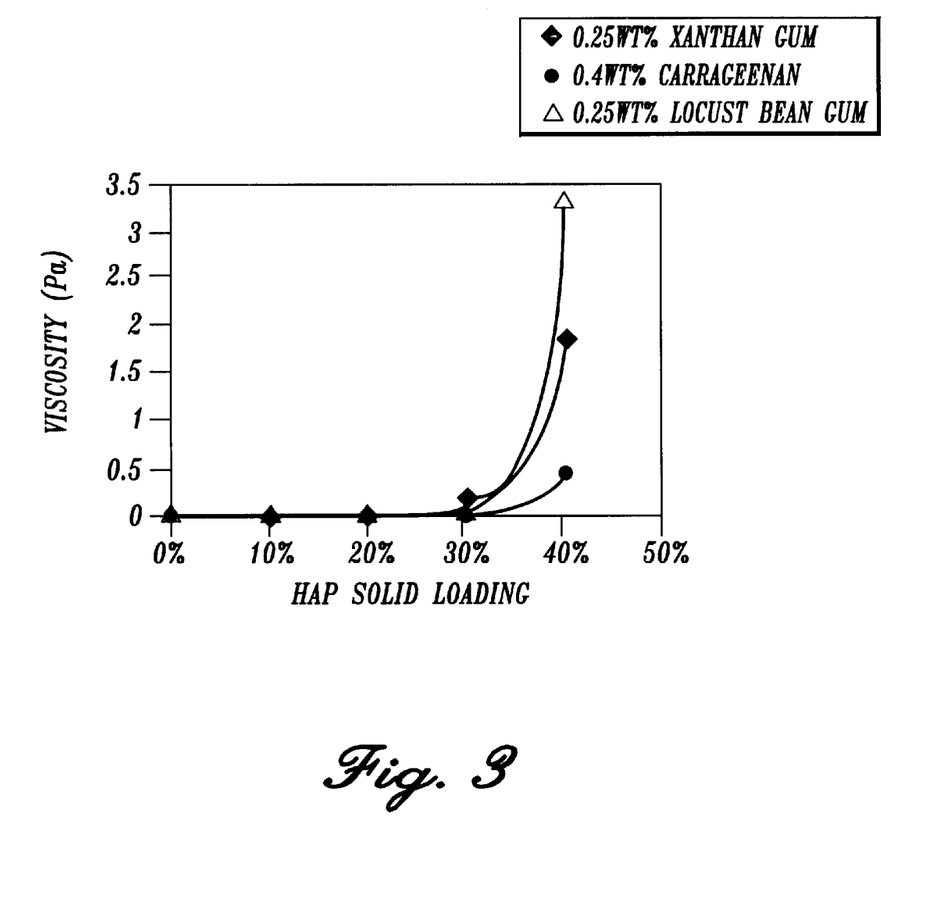
FIG. 3 is a plot of solids loading for three polysaccharide polymers.

Solids loading had a great influence on viscosity as illustrated in FIG. 2. The viscosity of these systems was almost constant with HAP solids loading equal or below 30 wt % as shown in FIG. 3. Further increasing the solids loading to 40 wt % dramatically increased the viscosity of the suspensions. As a matter of fact, the highest HAP loading achievable is about 43 wt %. Above that it became difficult to measure rheological properties.

Effect of temperature on gelation properties was also investigated. It is known that temperature up to 93° C. have no effect on the viscosity of xanthan gum solutions. Locust bean gum solution, prepared at 70–80° C., also showed no significant changes in viscosity as the temperature was decreased. K-carrageenan solution, prepared at 70–75° C. in a similar way to locust bean gum, formed a rigid gel upon cooling. Its rheological behavior was investigated as a function of temperature. Temperature dependent viscosity measurements of carrageenan were started at 70° C. and eventually cooled to 20–30° C. in a water jacket of the rheometer.

Figure 4:
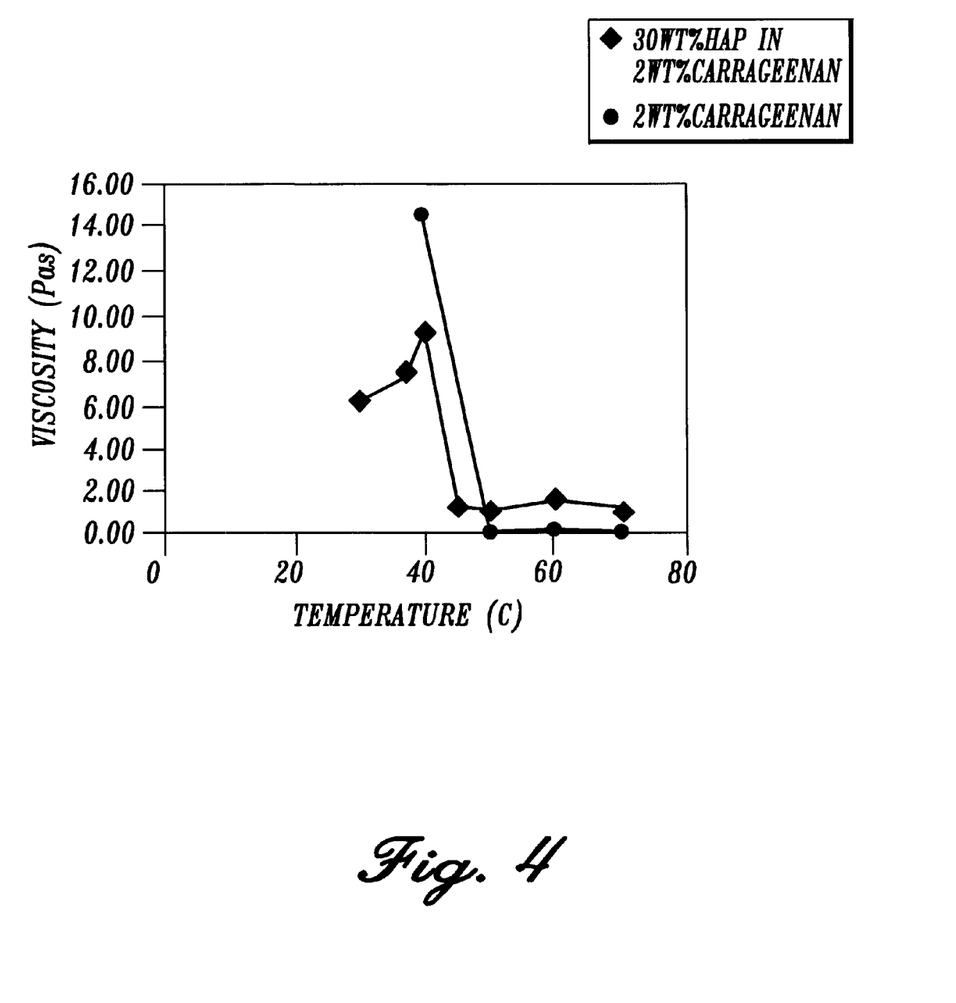
FIG. 4 is a plot of temperature against viscosity carrageenan and HAP carrageenan supensions.

As shown in FIG. 4 at higher temperature (50–70° C.), the suspension containing 30 wt % HAP and 2 wt % carrageenan had low viscosity values. It formed a gel around 40° C., indicated by the sudden increase of viscosity. Below 40° C., the gel was fractured by applied shear force, resulting in the decrease of viscosity. A 2 wt % carrageenan solution without HAP showed a similar temperature dependence (FIG. 4). This thermal gelaton property makes the HAP-carrageenan suspension a good candidate as self-setting bone filling materials. It was fluid-like and injectable above 45° C., and formed a rigid gel at body temperature of 37° C.

Materials Characterization

Figure 5A:
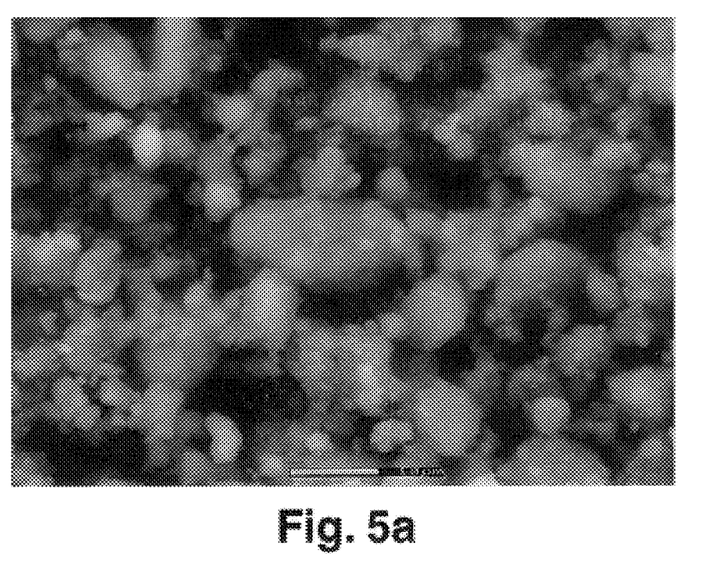
FIGS. 5a and 5b are Scanning Electron Micrographs showing the structures of 30 wt % HAP in 2 wt % carrageenan (a) and 40 wt % HAP in 2 wt % carrageenan (b).
Figure 5B:
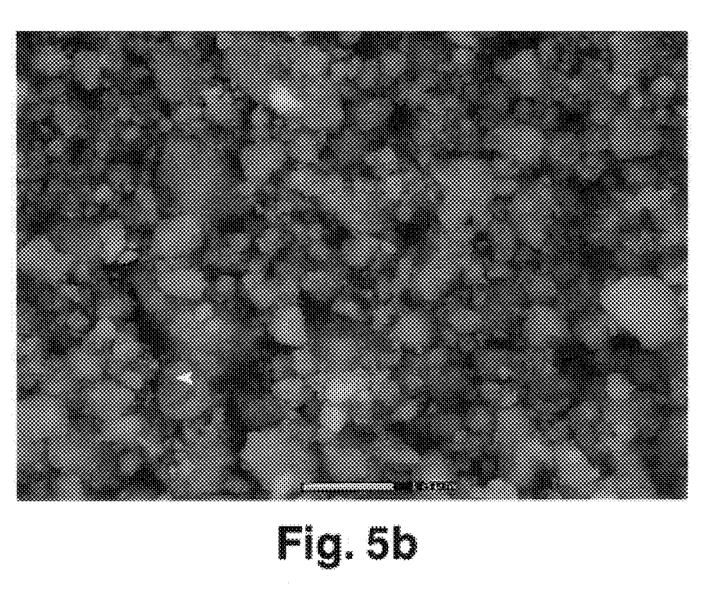

The microstructure and porosity of HAP-carrageenan pastes were studied by scanning electron microscopy (SEM). These pastes were prepared at 70–75° C. and cross linked in simulated plasma electrolyte solution as described above. They were then cut into small rectangular pieces with rough dimension of 2.5 cm×0.5 cm×0.3 cm. To preserve structures, they were quickly frozen in liquid nitrogen, then dried in vacuum at −12° C. for at least 24 hours. The dimension of each piece was measured using calipers before and after freeze drying to check on the shrinkage. While the samples containing 30 wt % or 40 wt % HAP and 2 wt % carrageenan showed less than 5% shrinkage, a sample containing 10 wt % HAP and 2 wt % carrageenan shrank 10–20%, indicating a structure collapse during freeze drying. The SEM images of 30 wt % and 40 wt % HAP in 2 wt % carrageenan are shown in FIG. 5. The structure of the 30 wt % HAP contained HAP agglomerates of 5–10 $\mu$m, and pores ranging from 5–15 $\mu$m throughout the monolith. An increase of HAP loading to 40 wt % produced denser material and reduced pore size to less than 5 $\mu$m.

HAP Dissolution By Constant Composition Method

Figure 6:
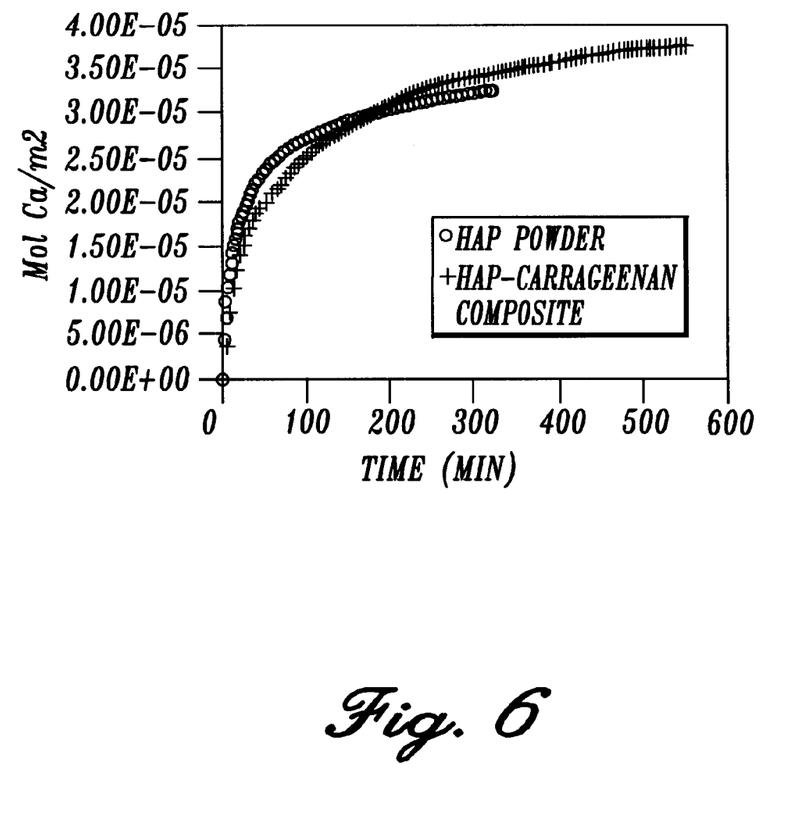
FIG. 6 is a plot of the dissolution of HAP/carrageenan composite and HAP powder at pH 6.5 in a solution containing 0.125 mM Ca $Cl_2$, 0.075 mM $KH_2PO_4$ and 0.15 M NaCl.

The kinetics of HAP dissolution of HAP-carrageenan pastes was studied by constant composition (CC) techniques. An undersaturated solution containing 0.125 mM $CaCl_2$ and 0.075 mM $KH_2PO_4$ and 0.15M NaCl was prepared by mixing stock solutions of 0.1M $CaCl_2$ and 0.1M $KH_2PO_4$ in 0.15M NaCl. The solution pH was adjusted to 6.5 using 0.1M KOH solution. Nitrogen, saturated with water vapor, was purged through the prepared solution to exclude carbon dioxide. A combination pH electrode (Corning) was used as a probe to monitor solution pH. An amount of 0.083 g of 30 wt % HAP-2 wt % carrageenan paste was weighed and added to the under saturated solution to initiate the dissolution experiment. The solution pH was kept constant by the potentiostatic controlled addition of 0.30M NaCl and 0.007M HCl. The rate of dissolution was calculated from the rate of addition of the acid after correcting for the volumes required to maintain constant pH. For comparison, the dissolution rate of 0.025 g HAP powder, same amount of HAP as in HAP-carrageenan paste, was measured using the same technique [FIG. 6]. The CC results indicated both samples have high initial rates, and dissolution slowed down as more and more calcium and phosphate ions accumulated in the solutions. HAP-carrageenan paste had a lower initial dissolution rate than the free HAP powders. As the carrageenan gradually leached out, the HAP-carrageenan paste became loosely attached and acted more like free particles.

Carrageenan Leaching Studies in Simulated Blood Plasma Electrolyte Solutions

Figure 7:
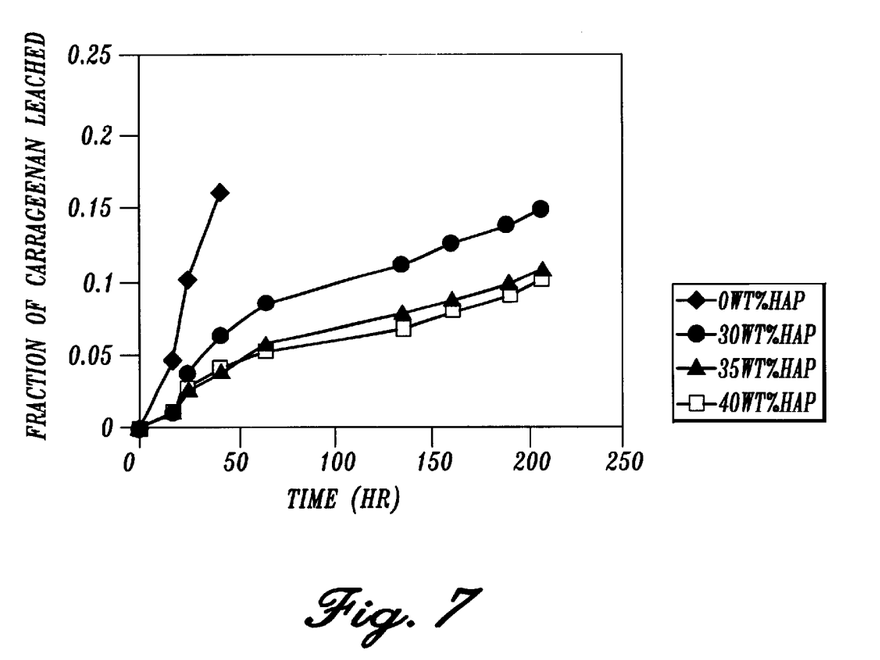
FIG. 7 is a plot of the fraction of carrageenan leached from the composition in a simulated blood plasma solution at 37° C. against time.

Suspensions containing 2 wt % carrageenan and 0 to 40 wt % HAP were prepared at 75° C. They were poured into small weighing dishes and formed blocks upon cooling to 37° C. After weighing each block (about 8 gram ), each block was placed in 20 ml of simulated blood plasma solution at 37° C. Periodically, the solution was collected and replaced with new solution. The HAP powder that was remaining in the solution was separated by centrifugation. The clear solution samples were diluted and mixed with methylene blue. The concentrations of carrageenan were determined by measuring adsorption at 559 nm against a standard calibration curve. The result is shown in FIG. 7.

Among the paste samples tested, those containing less than 20 wt % HAP were softened and broken down after 24 hours. Therefore, no data was available after this period. At higher HAP loading, the blocks maintained shape. The results indicated that as the HAP solid loading increased, the rate of carrageenan leaching decreased.

In vivo Results

Implants prepared according to the above procedure with carrageenan were placed in an induced bone defect in mice and produced an acute adverse response. Thus, while carrageenan is an attractive candidate material based on physical properties, it was found to lack biological compatibility when formulated as a polymer/ceramic composite. The high dissolution rate of carrageenan may contribute to the adverse response. Although the carrageenan illustrates the desireable physical properties of the invention, it may not be useful in the method of the invention if it is unsuited to implantation in a mammalian body.

EXAMPLE 2

Chitosan Study

Methods

High molecular weight (HMW) chitosan, $1.1–1.6 \times 10^6$ D, was purchased from Aldrich Chemical Company, Inc., low molecular weight (LMW) chitosan, 70 KD, was purchased from Fluka Chemie. Chitosans were dissolved in 0.1N HCl and purified before use by precipitation into acetone/water mixture. Hydroxyapatite (HAP), tricalcium phosphate (TCP), Bovine serum albumin (BSA), 5-fluorouracil (5-FU), were purchased from Sigma Chemical Company, and used as received. Phosphate buffered saline (PBS), pH 7.4 was used as a release medium in BSA and 5-FU release experiments.

Preparation of Chitosan-HAP and Chitosan-TCP Suspensions

Solutions containing 0.5–2 wt % of purified chitosan were prepared in 0.1N HCl. Chitosan-HAP or -TCP suspensions were prepared by simple mixing of the ceramic component with chitosan solution. Suspensions containing 20–45 wt % of HAP and 30–50 wt % of TCP were prepared.

Compressive Modulus Measurements

Experiments were performed using Dynamic Mechanical Analyzer equipped with the stainless-steel parallel plate measuring system. Compressive modulus was determined by using a uniaxial, unidirectional compressive deformation. The samples, in the form of cylindrical disks, were held in place initially with a minimal static stress, then the static stress was increased. The response of the sample (static strain) was used to calculate the static compressive modulus.

Release of Model Compounds

The release of 5-FU and BSA from chitosan-HAP or -TCP composites was conducted in PBS, pH 7.4 at 37° C. A cylindrically shaped samples of the composites were cured in a small diameter dialysis tubing. The amount of released compounds was determined by monitoring UV absorption of the release medium at 266 and 280 nm for the 5-FU and BSA, respectively. To maintain sink conditions, samples were transferred into fresh release medium at predetermined time intervals. The release kinetics data were reported as fraction of the total amount released versus time.

Results

In order to obtain chitosan-calcium phosphate composites suitable for the injectable, resorbable scaffolds for bone tissue regeneration, several properties of the composites need to be investigated and optimized. The most important requirements are the following: bio compatibility of the materials and their degradation products, injectability of the polymer-ceramic suspensions, suitable gelation kinetics of the composites, controlled degradation rates, ability to release small and large therapeutic agents and finally osteoconductivity. As a consequence of the above requirements, experiments have focused on the investigation and optimization of the following properties: rheological properties of the suspensions, and water content, porosity, compressive strength, and degradation rate of the cured composites. The ability of the composites to release therapeutic agents was also evaluated.

Chitosan-calcium Phosphate Suspensions: Preparation and Rheological Properties

Chitosan dissolves in diluted acids at pH 2–3 but the pH of the obtained solution may be titrated up to a pH of 6 with no change in polymer solubility. Therefore, chitosan-ceramic suspensions may be prepared at a wider pH range, i.e. 2–6. The pH of chitosan solution is important since it affects the solubility of the calcium phosphate phase of the composite.

Figure 8:
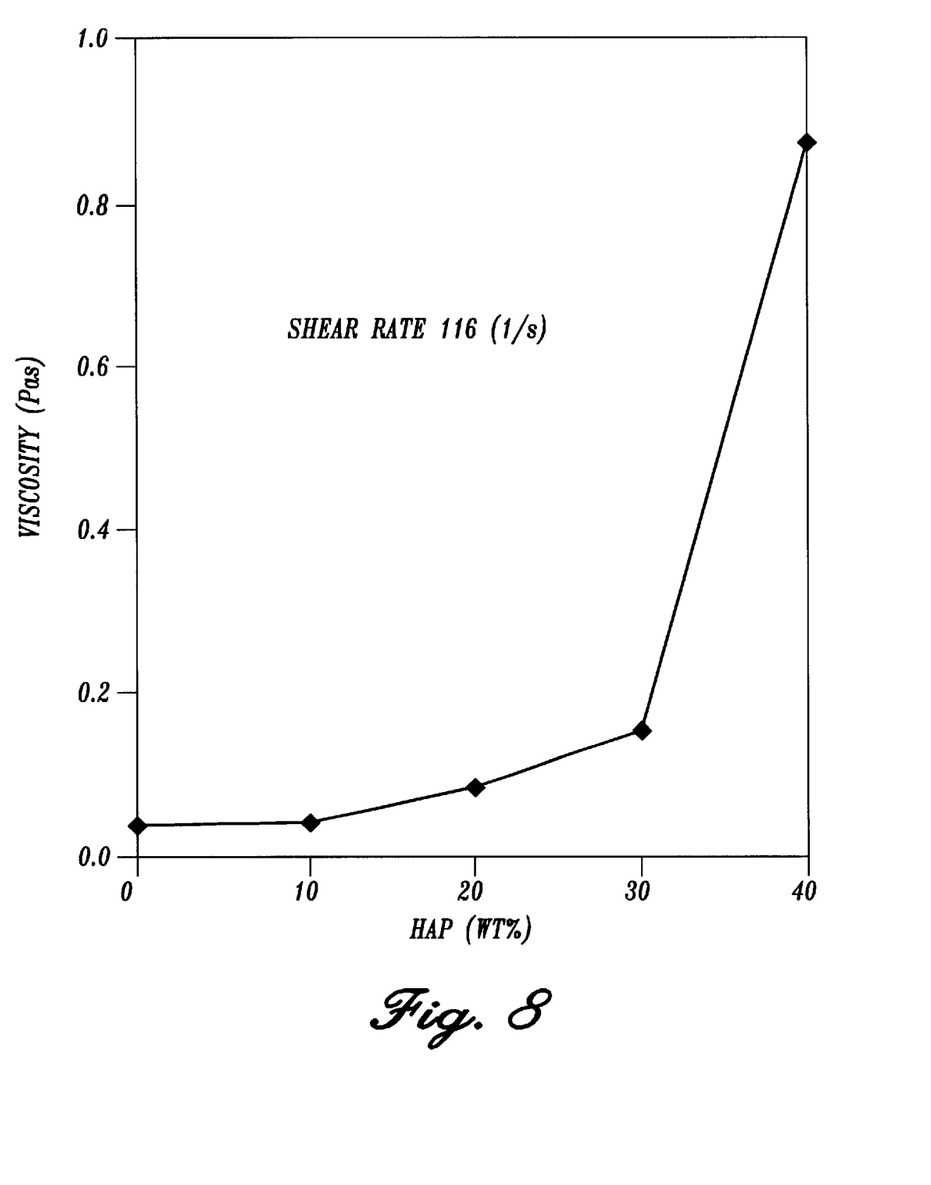
FIG. 8 is a plot of the viscosity of chitosan/HAP suspensions as a function of HAP wt % in 0.1N acetic acid.

Rheological properties of chitosan solutions and chitosan-calcium phosphate suspensions were investigated as a function of chitosan concentration, molecular weight, content and type of a calcium phosphate phase (HAP or TCP). As illustrated in FIG. 8, chitosan-HAP suspensions containing up to 40 wt % of HAP phase exhibited viscosities and flow suitable for injectable bone paste applications.

Compressive Modulus

Figure 9:
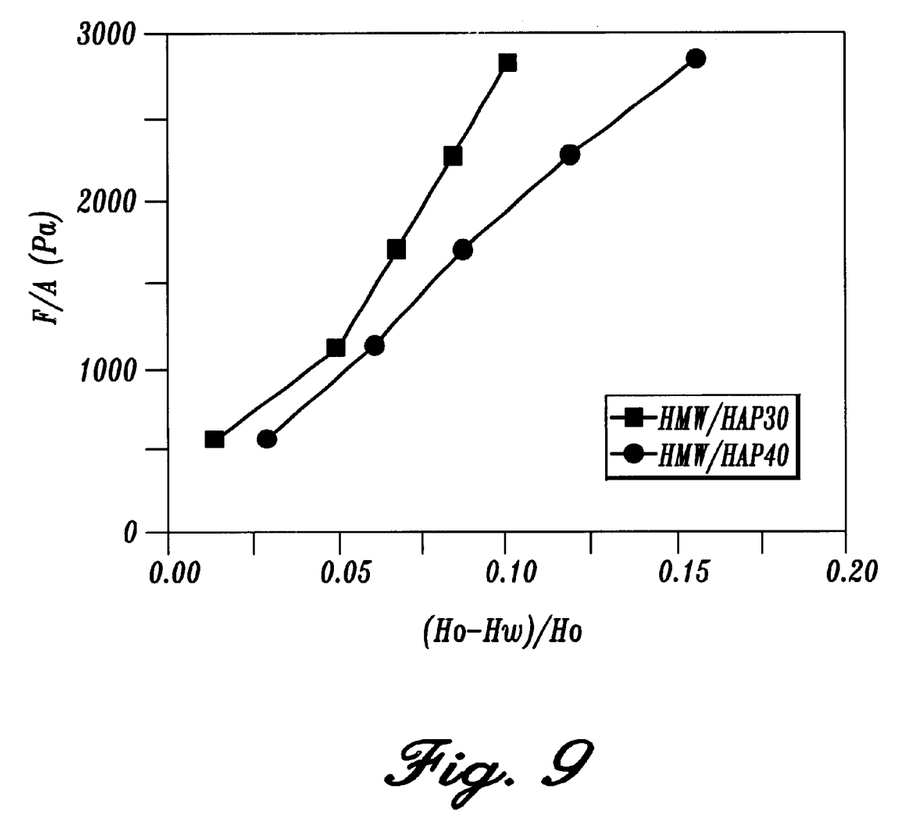
FIG. 9 is a plot of the compression modulus of chitosan/HAP composites showing the effect of solids loading.
Figure 10:
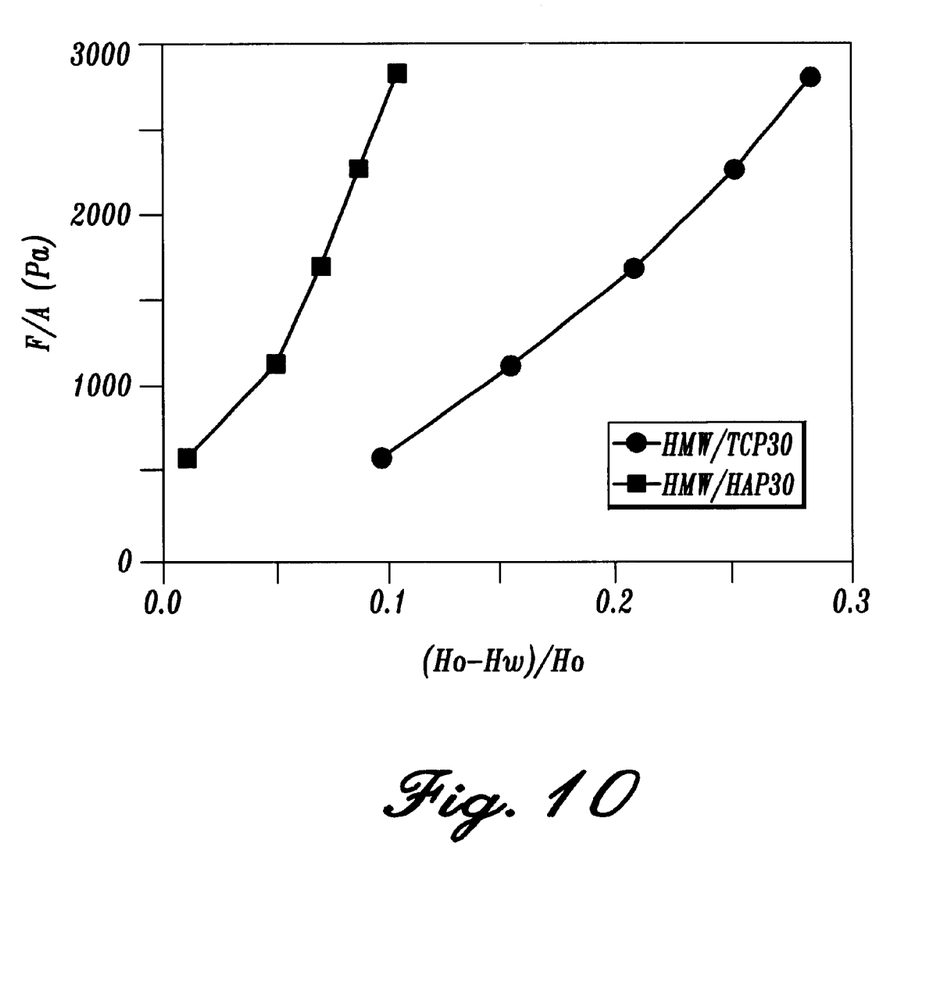
FIG. 10 is a plot of the compression modulus of HMW chitosan/HAP and chitosan/TCP showing the effect of the ceramic calcium phosphate phase.

Compressive modulus is a measure of the resistance of the sample to compression and is an indicator of stiffness or rigidity. Relative compression moduli were determined to assess the changes in mechanical properties of the polymer-ceramic composites resulting form the gelation of the polymeric component. The compressive moduli were determined for a series of polymer-ceramic composites differing in composition in terms of ceramic (HAP or TCP) as well as polymeric components (LMW or HMW chitosan). Results are presented in FIGS. 9 and 10. The effect of solids loading, i.e., the amount of ceramic phase in the composite, on the compressive modulus of HMW chitosan-HAP composite is illustrated in FIG. 9. Composites with higher solids loading, 40 wt %, demonstrated higher relative compressive modulus as demonstrated by a steeper slope of the stress strain curve. A similar trend was observed for the chitosan TCP composites. The effect of the ceramic phase type is illustrated in FIG. 10. Composites containing HAP demonstrated higher relative compressive moduli than composites containing TCP. The trend was similar for both chitosans HMW and LMW (results not shown). The results of compressive modulus studies clearly demonstrated that the chitosan-calcium phosphate composites in a gelled state maintain mechanical integrity in contrast to the flowable, injectable properties of the corresponding suspensions.

Release of Model Compounds

Different therapeutic and osteoconductive agents may be incorporated into the thermally reversible polymer-ceramic composites as needed. Examples of therapeutic agents include antibiotics for the local treatment of possible infections, anticancer agents for the site specific treatment of bone tumors. Examples of osteoconductive agents include growth factors and bone morphogenic proteins. In order to asses the possibility of using our novel polymer-ceramic composites as delivery vehicles for therapeutic and/or osteoconductive agents we have investigated the release of model low and high molecular weight compounds.

Figure 11:
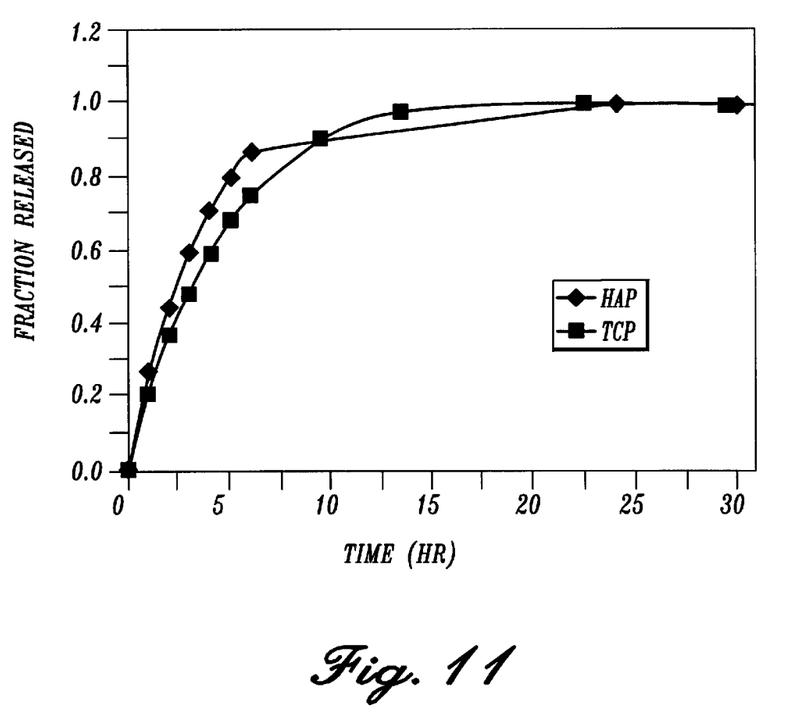
FIG. 11 is a plot of the release of 5-fluorouricil from chitosan/HAP and chitosan/TCP compositions.
Figure 12:
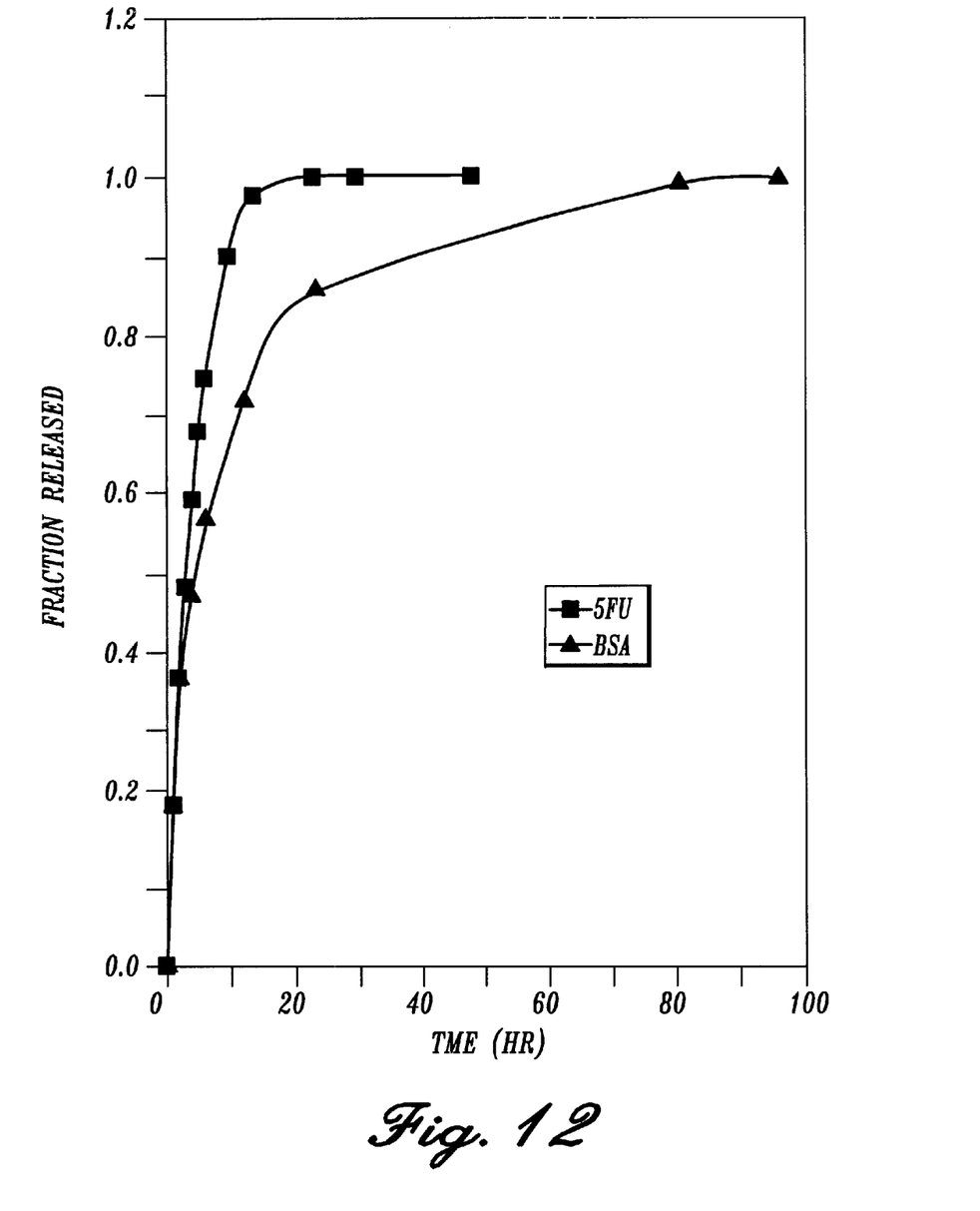
FIG. 12 is a plot comparing release of 5 fluorouricil and bovine serum albumin from a chitosan/HAP composition.

An anticancer agent, 5-fluorouracil (5-FU) was used as a model low molecular weight compound and bovine serum albumin (BSA) was used as a model macromolecule. The results of the release experiments are presented in FIGS. 11 and 12. In FIG. 11 the effect of two calcium phosphate ceramic phases are compared, showing a small rate advantage to HAP over TCP. As illustrated in FIG. 12 the release of 5-FU and BSA demonstrated different kinetics. While 5-FU released from the chitosan-TCP composite within 10 hours, BSA release was much less rapid and lasted for 40 hours. These results may be explained by the differences in the effective size of the releasing molecules. BSA, being a macromolecule demonstrated slower release kinetics due to the lower effective diffusion coefficient within the polymer-ceramic matrix. The release results demonstrated that chitosan-calcium phosphate composites may be used as a matrix for the release of therapeutic agents and proteins such as growth factors and bone morphogenic proteins.

We claim:

1. A composition, comprising:
a biologically compatible polymer that is soluble in water and which becomes insoluble in water and forms a gel at between 35° C. and 40° C. in response to a temperature change dissolved in an aqueous solvent and a biologically compatible ceramic component the composition being fluid under non-physiological conditions and non fluid under physiological conditions.

2. A composition according to claim 1, wherein the polymer is selected from the group consisting of resorbable polymers, non-resorbable polymers, natural polymers, and synthetic polymers.

3. A composition according to claim 1, wherein the polymer is selected from the group consisting of carrageenan and random copolymers of alkyl or pyrrolindine substituted methacrylamides with a hydrophilic comonomer and combinations thereof.

4. A composition according to claim 1 which further comprises a therapeutic agent.

5. A composition according to claim 4 wherein the therapeutic agent is selected from the group consisting of bone growth factors, antibiotics, chemotherapy drugs, radioisotopes, osteoconductive factors, bone morphogenic proteins and cytokines.

6. A composition according to claim 1 wherein said biologically compatible ceramic component comprises a hydroxyapatite ceramic, or a tricalcium phosphate ceramic or mixtures thereof.

7. A composition according to claim 1 which further comprises voids.

8. A composition according to claim 7 wherein the voids have a cross section in the range of 100 to 200 microns.

9. A method of forming a solid implant in a mammalian body which comprises the steps of mixing a biologically compatible gel forming polymeric component that is soluble in water and which becomes insoluble in water and forms a gel at between 35° C. and 40° C. in response to a temperature change with a biologically compatible ceramic or ceramic forming component providing a fluid mixture, and placing the fluid mixture dissolved in an aqueous solvent into a mammalian body wherein the fluid mixture gels after placement in the mammalian body in response to a stimulus provided by conditions present or induced in the mammalian body.

10. A method according to claim 9 wherein the polymer is selected from the group consisting of resorbable polymers, non resorbable polymers, natural polymers and synthetic polymers.

11. A method according to claim 10, wherein the polymer is selected from the group consisting of carrageenan and random copolymers of alkyl or pyrrolindine substituted methacrylamides with a hydrophilic comonomer and combinations thereof.

12. A method according to claim 9 which further comprises the step of mixing the therapeutic agent with the fluid mixture.

13. A method according to claim 12 wherein the therapeutic agent is selected from the group consisting of bone growth factors, antibiotics, chemotherapy drugs, radioisotopes, osteoconductive factors, bone morphogenic proteins and cytokines.

14. A method according to claim 9 which comprises the further step of mixing a material into the fluid mixture which produces voids in the gelled fluid mixture.

15. A method according to claim 9 wherein the material produces voids having a cross section on the order of 50 to 500 microns.

* * * * *